(12) United States Patent
Gao et al.

(10) Patent No.: US 6,752,810 B1
(45) Date of Patent: Jun. 22, 2004

(54) INSTRUMENT AND METHOD FOR PULLING AND TWISTING A TIE ONTO TWO SEPARATED ITEMS

(75) Inventors: Hua Gao, Fox Point, WI (US); James A. Rinner, Racine, WI (US)

(73) Assignee: Pilling Weck Incorporated, Horsham, PA (US)

( * ) Notice: Subject to any disclaimer, the term of this patent is extended or adjusted under 35 U.S.C. 154(b) by 106 days.

(21) Appl. No.: 10/158,470

(22) Filed: May 31, 2002

(51) Int. Cl.$^7$ .............................................. A61B 17/56
(52) U.S. Cl. ........................................ 606/103; 606/74
(58) Field of Search .................... 606/103, 74, 148; 140/93 R, 93.2, 117, 118, 119

(56) References Cited

U.S. PATENT DOCUMENTS

| | | |
|---|---|---|
| 1,120,575 A | 12/1914 | Wertz |
| 1,209,434 A | 12/1916 | Hayden |
| 1,304,620 A | 5/1919 | Steinkoenig |
| 1,365,649 A | 1/1921 | Bates |
| 1,463,869 A | 8/1923 | Campbell |
| 2,049,361 A | 7/1936 | Ericsson |
| 2,279,068 A | 4/1942 | Siebrandt |
| 2,291,413 A | 7/1942 | Siebrandt |
| 2,455,609 A | 12/1948 | Schieb |
| 2,657,718 A | 11/1953 | Greathouse |
| 3,273,605 A | 9/1966 | Ferrara |
| 3,507,270 A * | 4/1970 | Ferrier ........................ 600/481 |
| 3,759,302 A | 9/1973 | Attenborough |
| 3,865,155 A | 2/1975 | Spath |
| 4,512,346 A | 4/1985 | Lemole |
| 4,527,554 A | 7/1985 | Klein |
| 4,587,963 A | 5/1986 | Leibinger |
| 4,606,335 A | 8/1986 | Wedeen |
| 4,813,416 A | 3/1989 | Pollak |
| 4,880,038 A | 11/1989 | Meinershagen |
| 4,935,027 A * | 6/1990 | Yoon ........................... 606/146 |
| 4,966,600 A | 10/1990 | Songer et al. |
| 5,004,020 A | 4/1991 | Meinershagen |
| 5,116,340 A | 5/1992 | Songer |
| 5,127,448 A | 7/1992 | Hillestad |
| 5,275,383 A | 1/1994 | Wick |
| 5,312,410 A | 5/1994 | Miller |
| 5,417,698 A | 5/1995 | Green |
| 5,447,512 A | 9/1995 | Wilson |
| 5,449,361 A | 9/1995 | Preissman |
| 5,501,688 A | 3/1996 | Whiteside |
| 5,540,698 A | 7/1996 | Preissman |
| 5,601,572 A | 2/1997 | Middleman |
| 5,741,279 A * | 4/1998 | Gordon et al. .............. 606/144 |
| 5,752,551 A | 5/1998 | Trueblood |
| 5,772,663 A | 6/1998 | Whiteside |
| 5,810,832 A | 9/1998 | Blasingame |
| 5,830,234 A | 11/1998 | Wojciechowicz |
| 5,849,012 A | 12/1998 | Abboudi |
| 5,851,209 A | 12/1998 | Kummer |
| 5,935,133 A * | 8/1999 | Wagner et al. .............. 606/103 |
| 5,968,077 A | 10/1999 | Wojciechowicz |
| 6,045,551 A | 4/2000 | Bonutti |
| 6,045,561 A | 4/2000 | Marshall |
| 6,185,858 B1 | 2/2001 | Choron |
| 6,217,580 B1 | 4/2001 | Levin |
| 6,287,307 B1 | 9/2001 | Abboudi |
| 6,332,889 B1 | 12/2001 | Sancoff |
| D476,084 S * | 6/2003 | Gao et al. .................. D24/133 |
| 2003/0028202 A1 * | 2/2003 | Sancoff et al. .............. 606/144 |

* cited by examiner

Primary Examiner—Michael J. Milano
Assistant Examiner—Bradford C Pantuck
(74) Attorney, Agent, or Firm—Arthur J. Hansmann

(57) ABSTRACT

An instrument and method for applying a suture of stiff but bendable material, such as wire, to broken bone for closing and holding the break. Also, the instrument and method are for pulling and holding two items together with a tie. The instrument has two parts movable relative to each other for pulling the items or bone together and for twisting the suture onto the bone to hold it together. The suture is strung onto the instrument on the exterior thereof without having the suture extend through the instrument interior, so the surgeon can guide the suture and accurately string it. A crank is applied to twist the suture after the suture has been initially secured to the bone to hold the bone together.

22 Claims, 5 Drawing Sheets

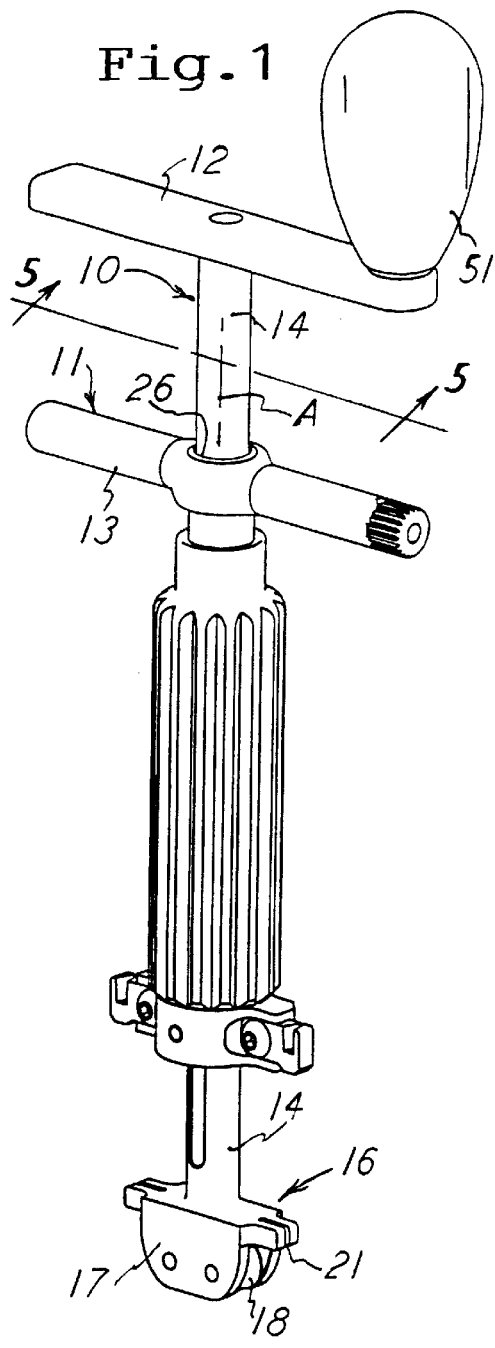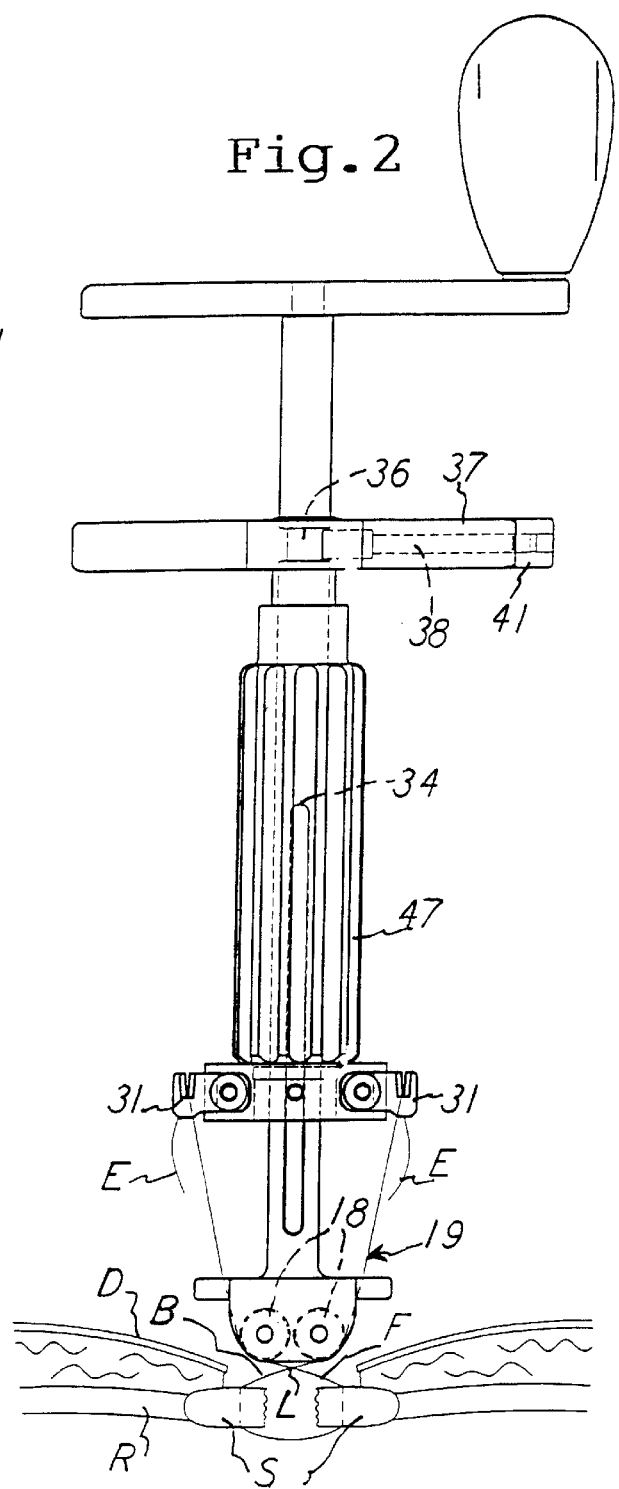

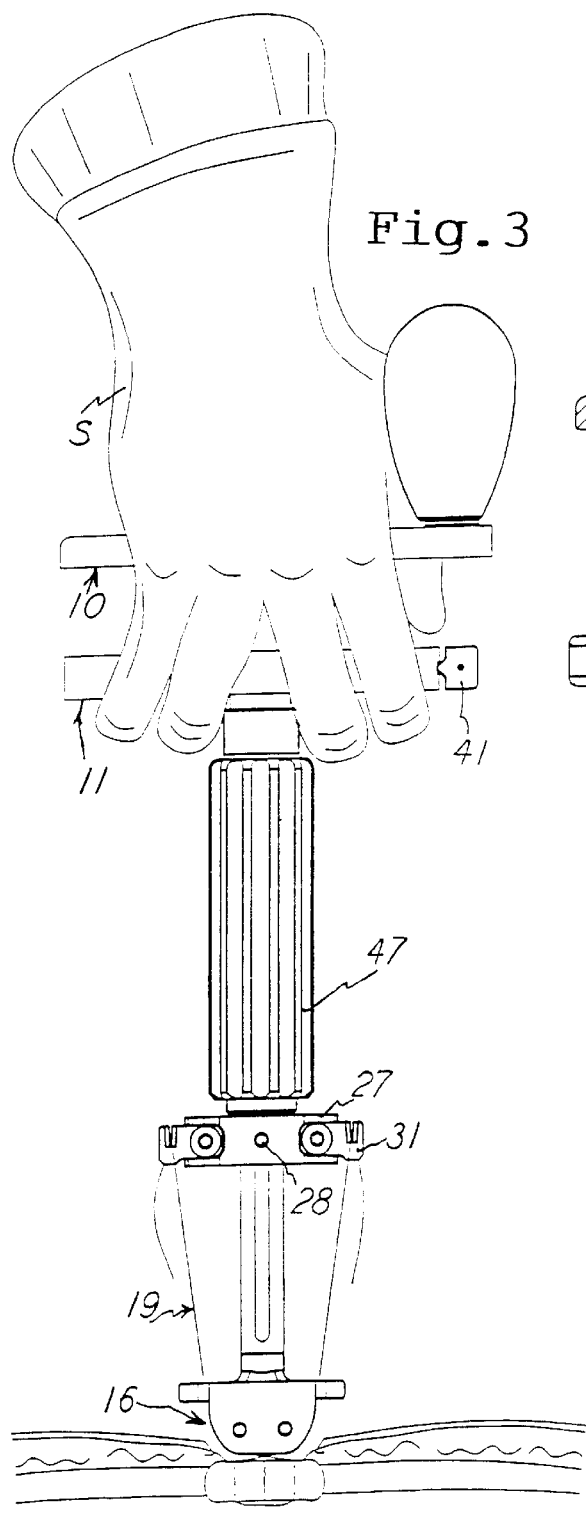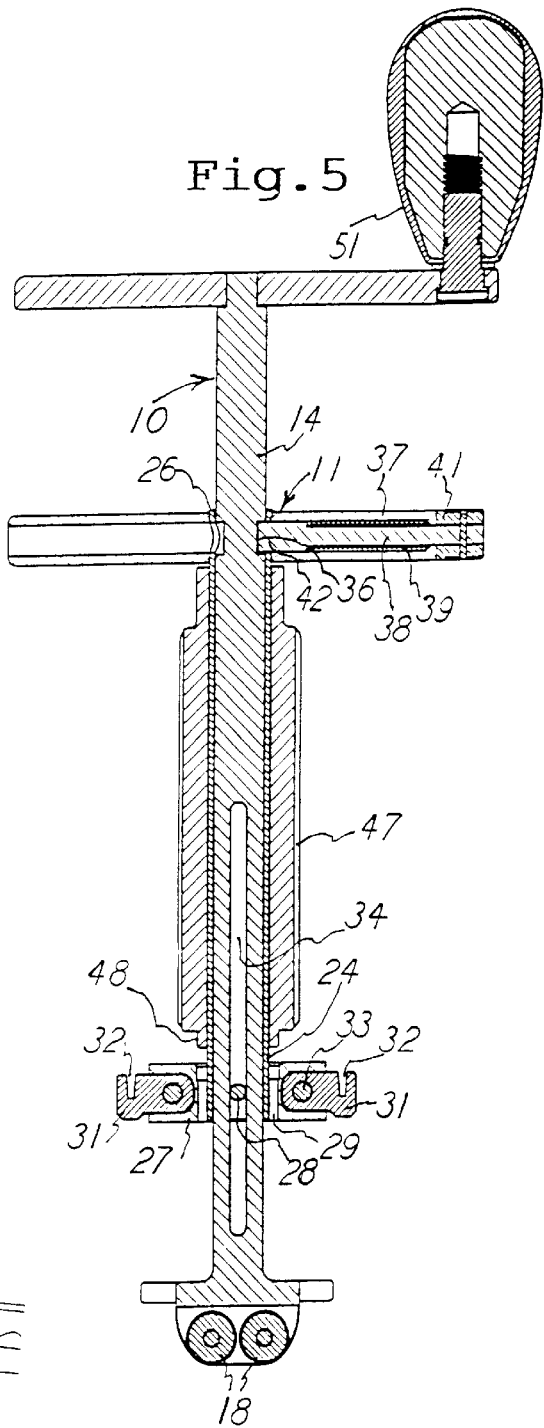

_US 6,752,810 B1_

INSTRUMENT AND METHOD FOR PULLING AND TWISTING A TIE ONTO TWO SEPARATED ITEMS

BACKGROUND OF THE INVENTION

Instruments and methods for applying a wire or strand to two items to hold the two items together are known in the prior art. Those instruments and methods apply relatively stiff strands, such as wire, to secure two items together when the strand is strung around the two items and is then twisted onto itself, such as in a helical pattern. The prior art is also aware of applying a wire or suture to broken bones to hold the bones together by twisting the suture onto itself.

Modern skeleton surgery is utilizing ways and means for applying mechanical items to the human skeleton to stabilize it. Where wire or like stiff suture material is applied there is a need for accurate and secure installation of the suture to the broken bone so that the bone is held together by the suture long after the surgery is finished.

The present invention improves upon the prior art by providing an instrument and method wherein a tie or suture can be readily and accurately installed on items or bones and then tensioned to draw the items or broken bones together and to ultimately twist the tie or suture onto itself in a helical pattern to tie the items or bone together. One example of this is with regard to closing the sternum of a patient who has had heart surgery where the sternum has been cut open and separated for access to the heart.

With this invention, the items or bones are drawn together in a completely firm manner and they are held together while the tie or suture is twisted onto itself. Thus, there is no slack or looseness in the tie or suture relative to the items or bone, and that is all accomplished in an efficient and rapid manner with optimum accuracy.

Compared to the known medical prior art of applying a wire to broken bone, in this invention the wire is strung at and connected to the exterior of the instrument and it is not strung through the interior of an instrument. Thus the stringing of the wire and attaching it to the instrument are easily and accurately accomplished. Also, the wire or suture is strung in a position to effect optimum pulling force on the bone for closing the broken bones onto themselves under easily applied tension to the suture.

In this invention, the tensioning of the suture onto the bone is accomplished by a squeezing action through the hand of the surgeon, and, with that same squeezing grip on the instrument, the surgeon can also twist the suture onto itself. No repositioning of the hand is required to perform both the tensioning and the initial twisting actions. With only one gripping action, the instrument is always under the accurate control of the surgeon for both the tensioning and the initial twisting.

Therefore, this invention accomplishes initially placing tension in the suture to draw the bones together, and it then twists the suture while holding that tension, and it then applies a cranking action to the suture for additional twisting of the suture. So the broken bones are securely positioned and then held there and secured together.

Other objects and advantages will become known upon reading the following description in light of the accompanying drawings.

BRIEF DESCRIPTION OF THE DRAWINGS

FIG. 1 is a perspective view of an instrument of this invention.

FIG. 2 is a side elevational view of FIG. 1 with a suture and a portion of a patient's body added thereto.

FIG. 3 is a view similar to FIG. 2 but with parts of the instrument in different positions and a portion of a patient's body and a surgeon's gloved hand added thereto.

FIG. 5 is a sectional view taken on the plane designated by the line 5—5 of FIG. 1 and with a part in a different position.

DETAILED DESCRIPTION OF THE EMBODIMENTS AND METHOD

The drawings show preferred embodiments of the instrument of this invention. The herein description of the embodiments will also enable one skilled in the art, such as an orthopedic surgeon, to understand the method of this invention, that is, the steps in applying a suture to broken bones of a skeleton.

Figure 4:
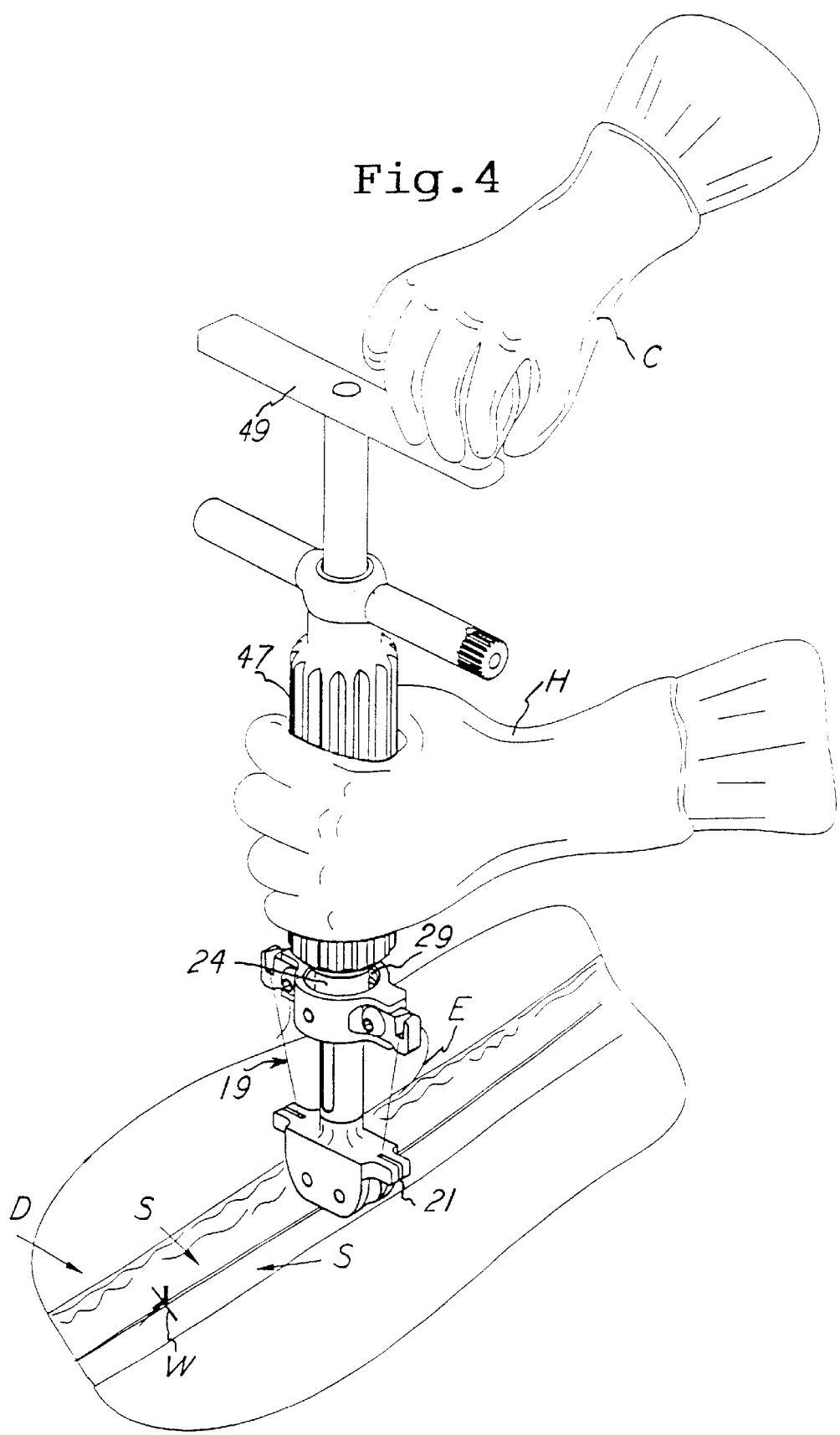
FIG. 4 is a perspective view similar to FIG. 1 but with a part in a different position and with a suture and the surgeon's two gloved hands and the portion of the patient's body added thereto.

FIGS. 2, 3, and 4 show the instrument being applied to a patient's sternum, such as after heart surgery where the sternum was separated for access into the chest cavity and to the patient's heart. Also, in this description and the claims, the reference to a suture should be understood to comprehend a metallic wire, such as stainless steel which is commonly used and which is of an appropriate gauge to be compatible with bone in this procedure of pulling and holding broken bones together. As such, the suture will be of a sufficient stiffness or self-suspending cantilever nature such that it can be strung relative to the instrument and the bone and that it can be twisted upon itself, as described herein.

The instrument herein includes a first part or handle 10 and a second part or handle 11, and those two parts are telescoped together and extend along a common axis A and are slidable therealong. Both parts 10 and 11 are T-shaped in that they include respective cross portions 12 and 13. Those cross portions are spaced apart to be within the span of the surgeon's hand, as seen in FIG. 3. and they are also within the hand span in the FIG. 2 positions of the parts 10 and 11 where they are further apart in their cross portions 12 and 13, compared to their FIG. 3 positions where the cross portions are closer together.

The first part 10 has a shaft or stem 14 extending throughout its length, and its lower end has a sheave assembly 16 thereon. The assembly 16 includes a mounting block 17 rigidly affixed to the shaft 14, and two sheaves 18 are rotatably mounted on the block 17 and they each have a slight circumferential depression surface therein for guiding a suture 19 therein, as seen in FIGS. 2, 3, and 4, Again, the suture 19 is preferably wire material capable of cantilever supporting itself, and being twisted upon itself, and to hold that twist or helical condition by itself.

Two suture guide slots 21 extend into the block 17 and are in line with the sheaves, as shown, and the suture extends through the slots to be slidable in the block 17 but are laterally restricted and guided thereby. In that respect, the first part 10 presents two facing walls 22 and 23 which are suture guides or abutment surfaces which form the slots 21.

Particularly FIG. 5 shows that the second part 11 has a cylindrical sleeve 24 affixed to the cross piece 13, such as by welding at 26, and the sleeve 24 is axially movably piloted on the shaft 14. The two parts 10 and 11 can slide up and down along the axis A and relative to each other, as seen in the orientation of the drawings.

An adaptor 27 is attached to the lower end of the sleeve 24 by means of a pin 28 extending through both the sleeve 24 and the adaptor 27. The adaptor 27 has a central opening 29 along the axis A which is oversized compared to the outer diameter of the sleeve 24 which it surrounds. To the extent of the oversize, there is space between the adaptor 27 and the sleeve 24 so the adaptor can limitly pivot relative to the sleeve 24 and about the mounting pin 28. That allows the adaptor to self-adjust relative to the suture 19 when tension is applied to the suture. Therefore, the suture will also self-adjust alone its entire length when it is being installed on the bone.

Figure 6:
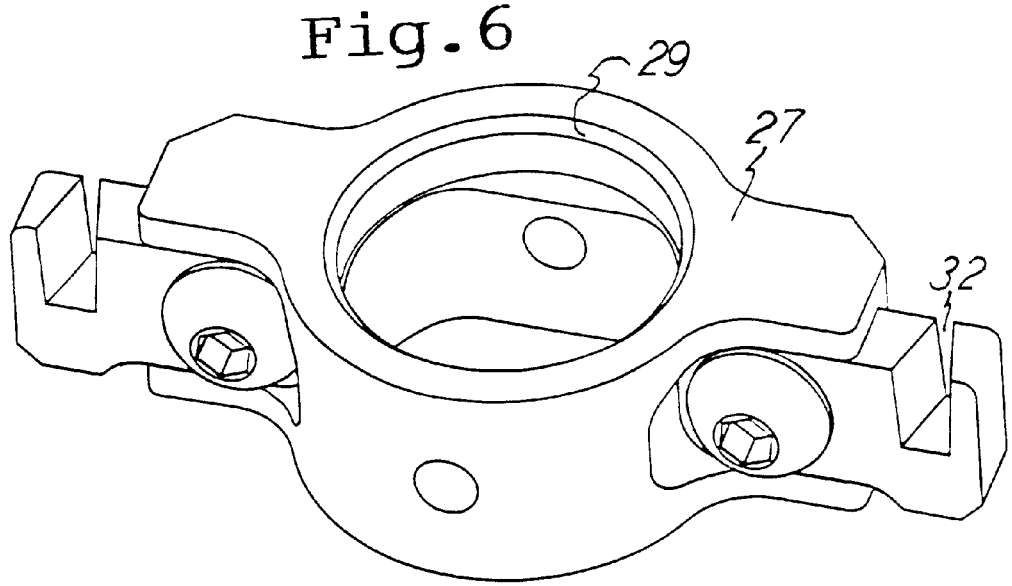
FIG. 6 is an enlarged perspective view of a part of the instrument as seen in FIG. 1.

Two suture grippers 31, have two V-shaped slots 32, in one embodiment and as seen in FIGS. 2, 4, and 6, and the slots 32 face upwardly and securely grip the suture in the V-slots to hold the suture without movement therein or any slipping therethrough. The grippers 31 are mounted on the adaptor 27 by mounting pins 33. Also, the grippers 31 are positioned on the plane transverse to the axis of the pin 28 for their pivoting.

A slot 34 extends axially along and completely through the shaft 14, and the pin 28 is slidably received in the slot 34. In that manner, the two parts 10 and 11 are telescopically slidable together and they are rotatable together.

FIGS. 2 and 5 show that the shaft 14 has a notch 36 at the intersection with the cross portion 13. The portion 13 includes a sleeve 37, which is the only part of the cross portion 13 that is welded to the sleeve 24, and a plunger 38 is slidable in the sleeve 37 to extend into latched engagement in the notch 36. A compression spring 39 forces on the plunger 38 to yielding urge the plunger 38 leftwardly into locked position with the shaft 14. When locked, the two parts 10 and 11 can not slide axially relative to each other, not until the plunger is released from its shown locked position in FIGS. 2 and 5.

To release the plunger 38, a knob 41 is rigidly fixed on the end of the plunger 38 which can be pulled outwardly along the sleeve 37 to where the plunger inner end 42 is released from the notch 36 in the shaft 14. When thusly retracted, rotation of the plunger 38 about its longitudinal axis will position a detent 43 onto the end surface 44 of the sleeve 37. Thus the plunger 38 can be pulled outwardly to where its inner end 42 is released from the notch 36 in the shaft 14, as seen in FIG. 3, and the detent 43 can then be positioned onto the sleeve end surface 44 to hold the plunger 38 in the released position.

When the detent 43 is not in the above-mentioned released position, the detent 42 is releasably disposed in a notch 46 on the end of the sleeve 37 so the plunger 38 can be in the engaged position with the shaft 14 for the desired restriction against axial movement between the two parts 10 and 11. It is that restricted relationship that is desired when the suture 19 is being strung onto both the bone and this instrument. When that stringing is accomplished, as shown in FIG. 2, then the two parts 10 and 11 can be released for their relative axial movement to the FIG. 3 position, and thus the consequent tightening of the suture on the bone.

So, in the FIG. 2 position, there is a sternum S shown in two broken parts which were separated by the surgeon. The patient's skin D and ribs R are also shown. With suitable technique and instruments, the suture 19 is strung into contact with the two bone parts, and the suture is crossed over onto itself at a location designated L. That portion of the suture below the instrument, as seen in FIG. 2, can be an intermediate portion of the length of the suture 19. The suture also has legs portions, which are shown to be in contact with the sheaves 18, and which extend up through the slots 21 and to the grippers 31.

Therefore, there is one length of the suture 19 extending between its two terminal ends designated E, and it is in contact with the sheaves 18 and is crossed over at the location L which is on the upright axis A. Which strand of the suture is crossed over closer to the front, as viewed in FIG. 2, is significant. That is, with the strand F extending at the front or nearest, as viewed in FIG. 2, the strand B is at the back or farthest, as viewed. At this time, it will then be noted that the instrument can be rotated one-half turn clockwise about the axis A, as view from above in FIG. 2, and that will then have the suture 19 twisted one full turn upon itself to thus be self-tied and secured. thus, each crossed strand of the suture 19 is re-directed back onto itself in a 180 degree turn to encircle and trap the other strand and thereby form a stabile hook with the other strand.

However, that one-half rotation is not performed until the instrument is in the FIG. 3 position, that is, when the two parts 10 and 11 have been moved relative to each other by squeezing therebetween, by a surgeon's gloved hand S, to place tension in the suture 19 and thereby draw the broken bones into closed relationship, as seen in FIG. 3. That is an initial twist of the suture 19. The squeezing by the surgeon's gloved hand and the one-half rotation are both performed without the need for the surgeon to reposition his hand on the instrument, therefore, it is facile and accurate.

In that action of twisting, the sheaves 18 and the walls 22 and 23 serve as guides for the suture 19 to transmit the twisting force on the suture 19. The sheaves are therefore disposed as close as possible to the bone, as seen in FIG. 3, so the helical twisting is close to the bone and along axis A.

After the surgeon has accomplished the FIG. 3 display, then the surgeon can grip the instrument with gloved hand H, as shown in FIG. 4. Thus there is a cylindrical handle 47 piloted on the instrument and telescopically extending over the sleeve 24 to be both axially movable and rotatable relative thereto. The instrument is thus hand-guided with the shown fluted handle 47 which is disposed centrally along the shaft 14 for optimum guidance and position-directing of the entire instrument, rather than having the handle 47 disposed on only the upper end of the shaft 14.

Also, between the FIGS. 2 and 3 position, the handle 47 is slightly raised to the FIGS. 4 and 5 position to where it does not contact the adaptor 27. The adaptor 27 has the central circular opening 29, forming an annulus with the lower end of the sleeve 24, for receiving the lower circular end 48 of the handle 47. In that lowered position of FIG. 3, the handle 47 stabilizes the adaptor 27 against its otherwise rocking or pivoting action. Thus, in the stringing of the suture 19 in the FIG. 2 position, the adaptor is stabilized and will not move relative to the remainder of the instrument. However, when the handle 47 is in the raised FIGS. 4 and 5 position, the adaptor 27 will then self-adjust by rocking about the axis of pin 28 to positions in response to the tension in the suture 19. The tension placed in the suture 19 produces a force on the adaptor, and the suture can be uniformly pulled upon for the ultimate suture twisting action explained hereinafter. The twisting is close to the bone and along the axis A.

To further twist the suture, There is a crank 49 fixed on the upper end of the shaft 14 to rotate the entire instrument, except for the handle 47 which the surgeon is holding, as seen in FIG. 4. Thus, the surgeon's gloved hand C grips the crank 49 by its knob 51, a rotation handle, to rotate the shaft 14 and the grippers 31 and the guides 18 and 22, 23. For that final twisting, the surgeon holds the instrument by the handle 47 and rotates the crank 49 to thereby form the second, and additional twists, if desired, in the suture 19. FIG. 4 also shows the completed twisted suture W in its final form and twist, and it is, of course, under the ultimately closed skin D.

Figure 7:
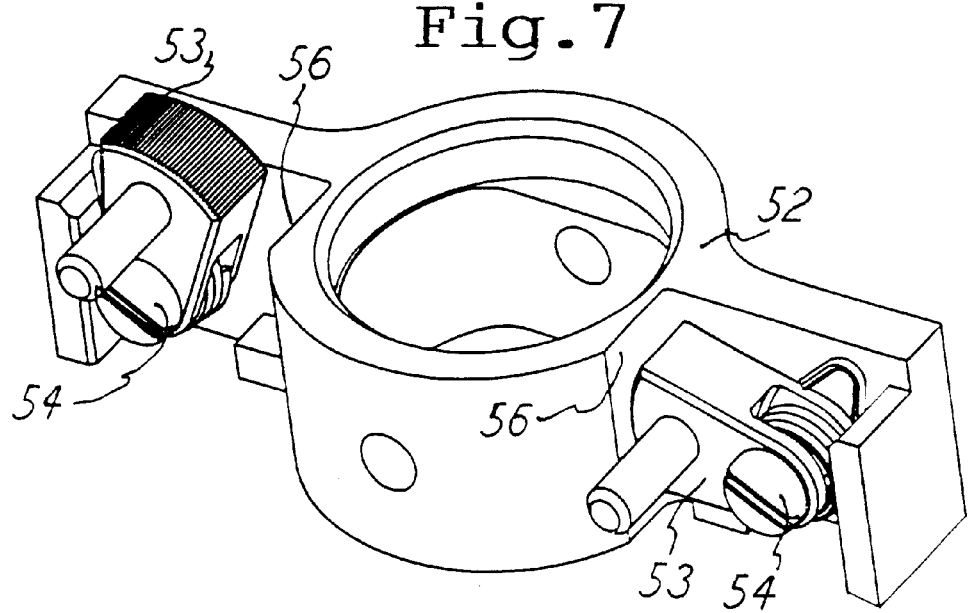
FIG. 7 is a perspective view similar to FIG. 6 but showing another embodiment of the part seen in FIG. 6.
Figure 8:
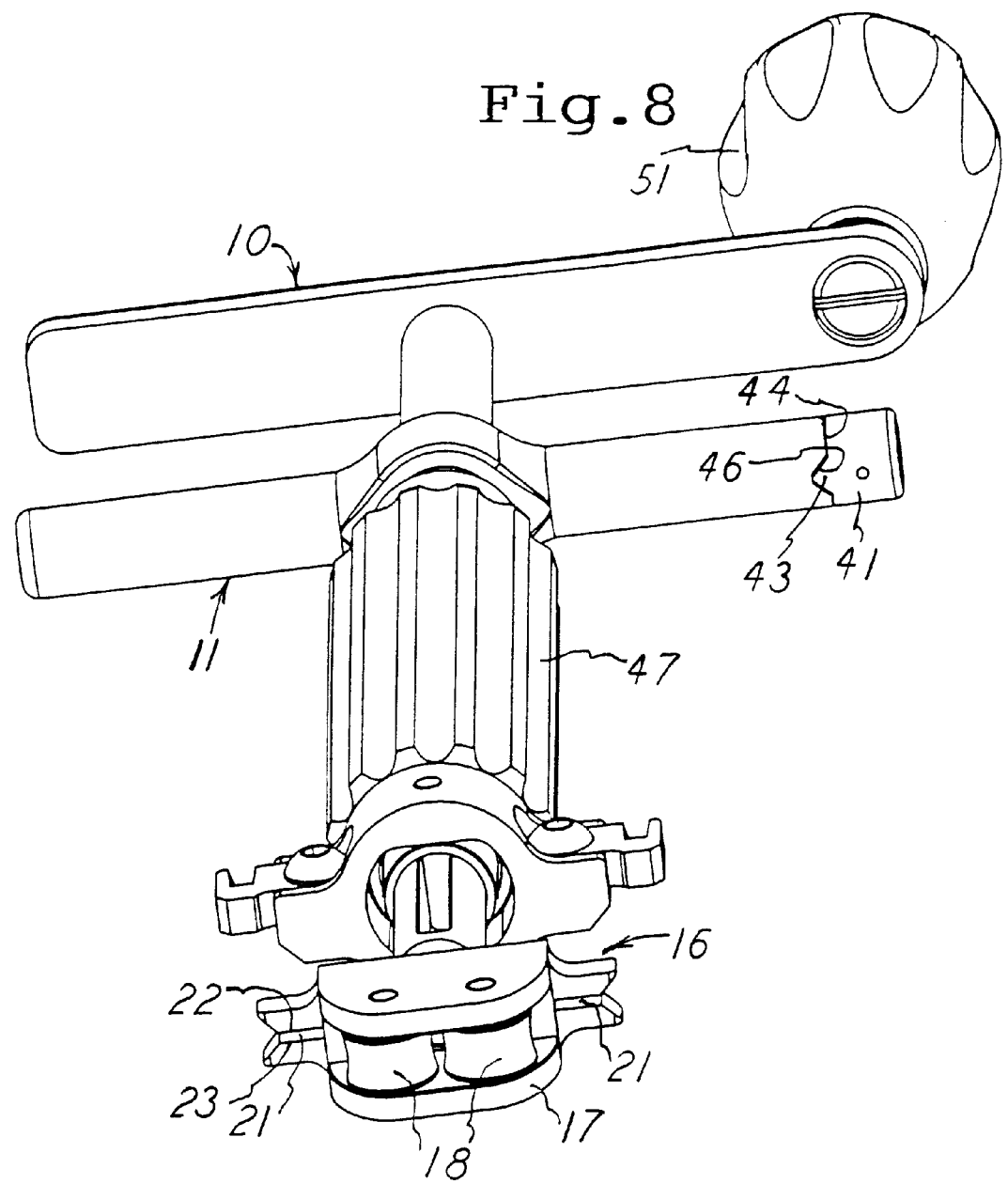
FIG. 8 is a bottom perspective view of the instrument of FIG. 1, with modifications of some parts thereof.

FIG. 7 shows another embodiment of the suture gripper, and here there is a substitute adaptor 52 which can replace the adaptor 27 and is mounted on the pivot pin 28, just as with the adaptor 27. However, instead of the wedge slots 32, there are two clamps 53 which are pivotally mounted on screw pins 54 to pivot into wire-contacting positions against walls 56 on the adaptor 52. The unshown suture would be trapped between the clamps 53 and the adjacent walls 56, just as the suture is trapped by the V-slots 32.

In summary, the suture 19 is strung onto the bone and the instrument, as seen in FIG. 2. That may be done by tools, including conventional surgeon's pliers and wire threaders. In doing so, the instrument is elongated to permit a good view of the work site by the surgeon, and it virtually has a pointed lower end at the block 17 to direct the instrument to the desired site. The cross-over of the suture on itself at L is in a certain relationship whereby there can be a hereinafter-mentioned rotation in a direction to cause the suture to have one full twist upon itself.

In that stringing of the suture, the wire two ends E can be bent down to be securely held in the grippers 31, and any excess can be cut off. Also, The handle 47 will automatically be in its lowered position in contact with the adaptor 27 to hold the adaptor level, as seen in the shown upright position of the instrument in FIG. 2.

Next, the latch at 36 can be released to have the two parts 10 and 11 be axially movable relative to each other.

Next, the two handles 10 and 11 can be squeezed to pull on the suture and thereby draw the bone together, as seen in FIG. 3. Then, with the same grip and continued squeezing by the gloved hand S to hold the bone together, the surgeon can rotate the instrument one-half turn, in that proper direction, to continue the aforementioned cross-over directional relationship and create the initial twist, or hook, in the suture 19.

That twisted suture then can, by itself, hold the bone together.

The surgeon can then raise the handle 47 to release it from the adaptor 27, as seen in FIGS. 4 and 5, and thereby allow the adaptor to pivotally adjust about its mounting pin 28 to provide for uniform tension in the suture 19 when tension is applied to the suture, such as in the next step.

In FIG. 4, the handle 47 and knob 51 can be gripped by the surgeon, and the instrument can then be mechanically rotated relative to the stationary and stabilizing handle 47 and about the axis A, and thereby form helical wire twists W with the twisted and cut-off suture, as seen in FIG. 4, to secure the broken bone.

With regard to the grippers shown in FIGS. 6 and 7, it will be understood that the bite of those grippers is within the cross-sectional size of the suture, such as the diameter of a round suture or wire. Thus, the V-shapes of the slots 32 can be such that each slot 32 is formed to have an apex or such, as seen in the slot lower end in FIG. 6, and the slot size in the apex vicinity is at least within the size of the suture or like wire for non-slipping gripping. With that, the surgeon can position the wire in the doubled-tapered, double V slots 32, preferably by the use of surgical pliers (unshown but conventional) while holding the pliers with one hand while holding the instrument with the other hand. The suture can then be forced into the slot taper by a downward force on the suture ends E to secure the suture in the slots. Finger placement of the suture could alternatively he employed.

As shown, the slots 32 are double V-shaped slots or V—V slots, as termed herein. That is, they are V-shaped in both the horizontal and vertical views, such as with FIG. 6, and they are therefore doubled tapered by having a taper in both the horizontal and vertical directions, for readily and securely receiving and holding the suture without slippage when the suture is under bone-closing tension.

FIG. 7 shows the cam clamp 53 and the wall 56 which contact the suture and are spaced apart in the gripping position to be within the size of the diameter of the suture therebetween, all to hold the suture readily and without slippage along the gripper, just as with the grippers 31.

The instrument and method are employable for any items that are to be pulled together and then held toward each other by the twisted tie.

It will be apparent to one skilled in the art that changes in the form of equivalent parts and method steps can be made relative to this disclosure. The scope of the claims should determine the extent of the patent protection.

What is claimed is:

1. A bone closer instrument for applying a suture onto two parts of bone which has a break along a plane extending perpendicular to the bone and along the break and with the perpendicular plane having a front direction and a rear direction therealong, comprising:

said instrument being arranged to receive a flexible suture which has a length with an intermediate portion disposable in clinching relationship with the bone two parts and with said length having two extending portions extending in opposite directions from said intermediate portion and crossing the perpendicular plane at a crossover location which is adjacent the bone and with each of said suture two extending portions having a terminal end, two instrument parts telescoped together and having a releasable lock therebetween and being constructed and related to be initially mechanically axially restrained in a first axially disposed telescopically collapsed fixed set relationship and being subsequently mechanically axially released of any mechanical restraint effective in either axial direction upon release of said lock to thereby be relatively axially movable for telescopically extending and be slideably movable relative to each other to a second relative axial position and with a first one of said two instrument parts fixedly gripping each said terminal end and a second one of said two instrument parts having surfaces in contact with said intermediate portions and being positioned between the perpendicular plane and said intermediate portions and away from the bone in the direction beyond the crossover location whereby holding each said terminal end and simultaneously moving said surfaces toward the bone causes said suture to draw the two parts of the bone together, a rotation handle on the instrument and connected with said two instrument parts and said surfaces for rotating said two instruments parts and said surfaces around the crossover location for twisting said suture onto itself, and a stationary stabilizing handle telescoped over and being non-rotatable on said two instrument parts for guiding said instrument during the rotation of said two instrument parts and said surfaces.

2. The bone closer instrument, as claimed in claim 1, wherein:

said suture intermediate portions and terminal ends are disposed on the exterior of said two instrument parts and are free of extending through said two instrument parts and are therefore available for the gripping and are exposed relative to said two instrument parts.

3. The bone closer instrument, as claimed in claim 1, wherein:

said two instrument parts are two handles disposed adjacent to each other within a spacing to be simultaneously gripped and squeezed by one hand of the operator to move said two handles relative to each other in the causing of said suture to draw the bone parts together.

4. The bone closer instrument, as claimed in claim 1, including:

said first one of said two instrument parts having suture grippers on the exterior to be available for respectively placing of each said terminal end onto a respective one of said grippers from the exterior of said first one of said two instrument parts.

5. The bone closer instrument, as claimed in claim 1, including:

said two instrument parts being rotatably connected together for uniform rotation by said rotation handle in the twisting of said suture.

6. A bone closer instrument for controlling a suture extending around two fragments of bone and with the suture extending from the bone in two suture ends, comprising:

two T-shaped handles with each having a stem and an elongated cross portion extending perpendicular to said stem, said stems being slideably telescopically related to each other along a longitudinal axis and being connected together to rotate in unison about said axis and having a releasable connection between said two stems for alternately releasing and locking said two stems relative to each other and relative to the slideable telescopic relationship therebetween for axially releasably restraining said stems in only one axially set relationship, which is a telescopically collapsed and set relationship, and said stems being free to move in either axial direction upon release of said releasable connection, a first one of said stems having a first set of two portions on said first stem for gripping the two suture ends in a spaced-apart relationship, a second one of said stems having a second set of two portions on said second stem for abutting the suture in two spaced-apart locations on the suture, said two sets being respectively connected to said stems for moving said two sets away from each other upon telescopically sliding said two stems relative to each other and thereby tension the suture relative to the bone to draw the bone fragments together after releasing said stop and moving said stems out of said collapsed and set relationship, and a third handle connected to said two handles for rotation of said two handles in unison and thereby twist the suture onto itself to tie the suture to the bone.

7. The bone closer instrument, as claimed in claim 6, wherein:

said first and said second two portions are respectively on the exterior of said two handles and are located thereon to be accessible from said exterior in the direction perpendicular to said axis for directly positioning the suture onto said two portions from the exterior of the instrument.

8. The bone closer instrument, as claimed in claim 6, wherein:

said two handles have a first end along said axis and said first and said second sets of said two portions are located adjacent said first end.

9. The bone closer instrument, as claimed in claim 6, wherein:

said first set of said two portions is movably supported on said first stem to be movable relative to said first stem while twisting said suture during rotation of said two handles.

10. The bone closer instrument, as claimed in claim 6, wherein:

said cross portions of said two handles are disposed adjacent each other for simultaneous gripping by a user's single hand and thereby allow single hand squeezing of said two cross portions toward each other in the tensioning of said suture.

11. The bone closer instrument, as claimed in claim 6, wherein:

said stems are slideably telescopically related by having a slot extending longitudinally axially along said first stem and having a pin on said second stem slideably received in said slot.

12. The bone closer instrument, as claimed in claim 6, wherein:

said stems are connected together to rotate in unison by having a pin and slot connection therebetween.

13. The bone closer instrument, as claimed in claim 6, wherein:

the suture is provided and consists of stainless steel wire of a rigidity capable of twisting upon itself into a helical pattern and self-retain that pattern in several complete loops of twist.

14. A bone closer instrument for controlling a suture extending around two fragments of bone and with the suture extending from the bone in two suture ends, comprising:

two T-shaped handles with each having a stem and an elongated cross portion extending perpendicular to said stem, said stems being slideably telescopically related to each other along a longitudinal axis and being connected together to rotate in unison about said axis and having a stop operative between said stems for axially releasably restraining said stems in only one axially set relationship, which is a telescopically collapsed and set relationship, and said stems being free to move in either axial direction upon release of said stop, a first one of said stems having a first set of two portions on said first stem for gripping the two suture ends in a spaced-apart relationship, a second one of said stems having a second set of two portions on said second stem for abutting the suture in two spaced-apart locations on the suture, said two sets being respectively connected to said stems for moving said two sets away from each other upon telescopically sliding said two stems relative to each other and thereby tension the suture relative to the bone to draw the bone fragments together after releasing said stop and upon moving said stems out of said collapsed and set relationship, a third handle connected to said two handles for rotation of said two handles in unison and thereby twist the suture onto itself to tie the suture to the bone, and a fourth handle telescoped over said two stems and being rotatably stationary thereon for stabilizing said instrument during the rotation of said two handles.

15. The bone closer instrument, as claimed in claim 14, wherein:

said first set of said two portions and said fourth handle have interengaging surfaces for stabilizing said first set of said two portions while manipulating said two sets relative to each other in drawing the bone fragments together.

16. A bone closer instrument for controlling a suture extending around two fragments of bone and with the suture extending from the bone in two suture ends, comprising:

two T-shaped handles with each having a stem and an elongated cross portion extending perpendicular to said stem, said stems being slideably telescopically related to each other along a longitudinal axis and being connected together to rotate in unison about said axis and having a releasable connection between said two stems for alternately releasing and locking said two stems relative to each other and relative to the slideable telescopic relationship therebetween for axially releasably restraining said stems in only one axially set relationship, which is a telescopically collapsed and set relationship, and said stems being free to move in either axial direction upon release of said releasable connection, a first one of said stems having a first set of two portions on said first stem for gripping the two suture ends in a spaced-apart relationship, a second one of said stems having a second set of two portions on said second stem for abutting the suture in two spaced-apart locations on the suture, said two sets being respectively connected to said stems for moving said two sets away from each other upon telescopically sliding said two stems relative to each other and thereby tension the suture relative to the bone to draw the bone fragments together after releasing said stop and moving said stems out of said collapsed and set relationship, a third handle connected to said two handles for rotation of said two handles in unison and thereby twist the suture onto itself to tie the suture to the bone, the suture having an overall length from and between said two end extensions and having an intermediate portion along the length, and two suture guides on said second one of said stems and located adjacent said second set of said two portions for engaging and guiding the suture intermediate length in the twisting of the suture.

17. An instrument for closing two fragments of broken bone by applying a suture having a wire characteristic of being capable of being twisted upon itself and to self-retain the twist and thereby form a tie to hold the bone fragments together, comprising:

said instrument being arranged to receive a flexible suture which has a length with an intermediate portion disposable in clinching relationship with the bone fragments and with said length having two extending portions extendable from said intermediate portion and being capable of crossing over each other at a crossover location which can be adjacent the bone and with said suture two extending portions being capable of terminating in two terminal ends, two instrument parts having a longitudinal axis and being telescoped together and telescopically movable relative to each other and having a lock therebetween for providing a physically axially secured position for repeatedly establishing a set maximum telescopically collapsed relationship and with side lock being releasable and thereby having said two parts freely telescopically movable away from said secured position, two suture grippers on a first one of said parts and with each having a V-shape for securely gripping said two terminal ends to hold said ends away from the bone, a second one of said two parts having surfaces contactable with said intermediate portions of said suture for guiding said intermediate portions for simultaneously moving said surfaces toward the bone to cause said suture to draw the two fragments of the bone together, a rotation handle on the instrument and connected with said surfaces for rotating said surfaces around the cross-over location for twisting said suture onto itself, and a stationary stabilizing handle telescoped over said two instrument parts for guiding said instrument during the rotation of said instrument parts and said surfaces for the twisting of said suture.

18. The instrument for closing two fragments of broken bone by applying a suture, as claimed in claim 17, wherein:

said grippers are V-shaped in two views thereof which are taken at right angles to each other to thereby have each of the grippers with two V-shapes.

19. The instrument for closing two fragments of broken bone by applying a suture, as claimed in claim 18, wherein:

said two V-shapes have a common apex.

20. An instrument for closing two fragments of broken bone by applying a suture having a wire characteristic of being capable of being twisted upon itself and to self-retain the twist and thereby form a tie to hold the bone fragments together, comprising:

said instrument being arranged to receive a flexible suture which has a length with an intermediate portion disposable in clinching relationship with the bone fragments and with said length having two extending portions extendable from said intermediate portion and being capable of crossing over each other at a crossover location which can be adjacent the bone and with said suture two extending portions being capable of terminating in two terminal ends, two instrument parts having a longitudinal axis and being telescoped together and telescopically movable relative to each other and having a lock therebetween for providing a physically axially secured position for repeatedly establishing a set maximum telescopically collapsed relationship and with said lock being releasable and thereby having said two parts freely telescopically movable away from said secured position, two suture grippers rockably mounted on a first one of said parts for securely gripping said two terminal ends to hold said ends away from the bone and for adjusting tension along said suture and between said suture two terminal ends upon rocking of said grippers, a restricting surface on said two parts for movement into and out of contact with said grippers for respectively precluding and freeing the rocking of said grippers, a second one of said two parts having two abutment surfaces contactable with said intermediate portions of said suture for guiding said intermediate portions for simultaneously moving said abutment surfaces toward the bone to cause said suture to draw the two fragments of the bone together, and a rotation handle on the instrument and connected with said abutment surfaces for rotating said abutment surfaces around the crossover location for twisting said suture onto itself.

21. The instrument for closing two fragments of broken bone, as claimed in claim 20, including:

a stabilizing handle telescoped over said two instrument parts for guiding said instrument during the rotation of said instrument parts and said abutment surfaces for the twisting of said suture, and said stabilizing handle being axially movable relative to said two instrument parts and having said restricting surface thereon for the movement into and out of contact with said grippers.

22. The instrument for closing two fragments of broken bone by applying a suture, as claimed in claim 20, wherein:

said grippers are V-shaped in two views thereof which are taken at right angles to each other to thereby have each of the grippers with two V-shapes.

* * * * *